United States Patent [19]

Tuchinskiy

[11] Patent Number: 5,774,779
[45] Date of Patent: Jun. 30, 1998

[54] MULTI-CHANNEL STRUCTURES AND PROCESSES FOR MAKING SUCH STRUCTURES

[75] Inventor: Ley J. Tuchinskiy, Tucson, Ariz.

[73] Assignee: Materials and Electrochemical Research (MER) Corporation, Tucson, Ariz.

[21] Appl. No.: 743,731

[22] Filed: Nov. 6, 1996

[51] Int. Cl.[6] .............................. B22F 3/12; C04B 38/04; C04B 38/06

[52] U.S. Cl. ........................ 419/2; 419/3; 419/4; 419/37; 419/41; 419/45; 419/54; 419/55; 264/56; 264/59; 264/63; 501/81; 501/95; 501/99; 425/550

[58] Field of Search ................................. 419/2, 3, 4, 37, 419/41, 45, 54, 55; 264/56, 59, 63; 501/81, 95, 99; 428/550

[56] References Cited

U.S. PATENT DOCUMENTS

| | | | |
|---|---|---|---|
| H721 | 1/1990 | McQuillan | 264/56 |
| 4,919,871 | 4/1990 | Lin et al. | 264/82 |
| 4,965,245 | 10/1990 | Sugimoto et al. | 505/1 |
| 5,171,735 | 12/1992 | Chien | 505/1 |
| 5,407,619 | 4/1995 | Maeda et al. | 264/63 |
| 5,433,904 | 7/1995 | Noky | 264/40.1 |
| 5,445,786 | 8/1995 | Harada et al. | 419/2 |
| 5,534,219 | 7/1996 | Marancik et al. | 419/4 |
| 5,547,623 | 8/1996 | Barnard | 264/82 |

*Primary Examiner*—Charles T. Jordan
*Assistant Examiner*—Daniel Jenkins
*Attorney, Agent, or Firm*—Jerome M. Teplitz

[57] ABSTRACT

A method for making multi-channel structures suitable for use as filters, catalyst carriers or the like.

A composite rod comprising an outer shell and an inner core is formed of respective mixtures of powders. The mixture for the outer shell comprises a sinterable powdered structural material such as ceramics, metals, intermetallics, and a powdered binder such as paraffin, wax or polymer. The inner core comprises a powdered channel-forming filler material such as melamine or polymers, or soluble inorganic compounds or a metal that can differentially be removed from the structural material of the shell.

The composite rod may be deformed, as by extrusion, to reduce its diameter. In any event, a bundle of composite rods is assembled and deformed, as by extrusion, to reduce the diameter of the bundle and of its component composite rods. Further bundles of the reduced diameter bundles of composite rods may be likewise deformed by extrusion to reduce further the diameter of the component composite rods of the successive bundles, thereby also increasing the number of such rods per given cross section area of the bundle. The final assembly of bundles is consolidated and the binder is removed, as by heating, followed by removal of the inner cores of the composite rods of the assembly of bundles and sintering of the remaining structure of ceramic or metal, as the case may be. In certain embodiments, the material of the inner core may be removed by heating it in the course of heating the structure to perform the sintering step. In other embodiments, the binder and/or filler material may be removed by means of a suitable solvent.

127 Claims, 2 Drawing Sheets

STEP 4

FIG. 5a

STEP 4

FIG. 5b 5,774,779

MULTI-CHANNEL STRUCTURES AND PROCESSES FOR MAKING SUCH STRUCTURES

The present invention relates to novel methods for producing multi-channel structures and to structures produced by such methods that are suitable for uses as filters, catalyst carriers, heat exchangers, etc., especially such structures having relatively small channels or apertures ranging from a few microns to a few millimeters in diameter.

BACKGROUND OF THE INVENTION

Various methods are known for making channeled materials. J. Reeman, R. W. Buswell and D. G. Ainley described the method of producing cooling passages in high-temperature turbine blades by the incorporation of cadmium wires in the blade pressing and their subsequent removal by evaporation during sintering, as reported and cited in "Fundamental Principles of Powder Metallurgy" edit by W. D. Jones, and published by Edward Arnold Publisher Limited, London 1960, page 341. This method is very labor and time consuming and does not allow the manufacture of micro-channeled materials with small and uniformly distributed channels.

A directional solidification method called GASAR has been developed for producing solids with controlled porosity [1–3] as disclosed in U.S. Pat. No. 5,181,549 issued Jan. 26, 1993. Metals are melted in a given atmosphere of a gas (usually hydrogen), poured into a mold while subjected to a desired pressure, and cooled. As the metal solidifies, the solubility of the dissolved gas goes through a sharp decrease and bubble nucleation occurs. Bubbles which form in the liquid float to a hotter region and are reabsorbed. Bubbles which form at the solid-liquid interface may grow as either isolated or continuous porosity, depending on the solidification conditions. The final microstructure of the porous materials depends on both thermodynamic and kinetic processes. Homogeneous nucleation of bubbles under GASAR processing conditions is impossible, the process is limited to systems which do not form hydrides, the eutectics are highly asymmetric, which leads to an extremely small range of compositions and solidification temperatures where stable eutectic growth is possible. This method does not allow the manufacture of long structures with through microchannels of a given diameter. Moreover, this method cannot be used for producing channels oriented in two or more desired directions.

U.S. Pat. No. 4,818,264 issued Apr. 4, 1989 to Marsha L. Langhorst discloses that hollow glass fibers have been made by drawing down tubes which can be used to produce glass polycapillary materials. Seven glass tubes, 1.8 mm outside diameter by 1.4 mm inside diameter, were placed inside an 8 mm outside diameter by 6 mm inside diameter glass tube and this assembly was drawn with a glass tube drawing machine. The subject patent cites an article by H. D. Pierce Jr. et al, Technical note "A method for the Preparation of Glass Multicapillary Columns", vol. 17, J. of Chromatographic Science, May, 1979, 297, as the source of this work. This method cannot be applied to the powder or brittle materials, such as ceramics, intermetallics, carbon, etc.

Extrusion method for forming thin-walled honeycomb structures was developed by D. Rodney et al. as disclosed in U.S. Pat. No. 3,790,654 issued Feb. 5, 1974. Rodney et al. disclose the use of an extrusion die having an outlet face provided with a gridwork of interconnected discharge slots and inlet face provided with a plurality of feed openings extending partially through the die in communication with the discharge slots. Extrudable material is fed to the die under pressure wherein the extrudable materials flow to the interconnected discharge slots communicating with the outlet face, wherein a portion of the material flows laterally within such slots to form a continuous mass before being discharged longitudinally therefrom to form a thin-walled structure having a multiplicity of open passages extending therethrough. The longitudinally discharged mass is rigidified to prevent deformation of the passages. The disadvantage of this method is a very complicated and very expensive tooling, which does not allow the production of the channels less than 0.5–1 mm in diameter and interchannel walls less than 0.2 mm in diameter, nor does it allow the production of structures with channels oriented in two or more directions.

Although not concerned with the manufacture of channeled materials, it is noted that some of the procedures used in carrying out the present invention to produce channeled structures, are also used in making monolithic fibrous ceramic structures, as described in U.S. Pat. No. 4,772,524 issued Sep. 20, 1988 to William S. Coblenz.

The Coblenz patent discloses a method of producing fibrous monolithic ceramic product of high density. This product is formed of a plurality of coated fibers and each coated fiber comprises a ceramic core with a ceramic coating. The green body of ceramic materials from which the product is formed is plastically deformed and densified by sintering. However, there is no disclosure or suggestion in this patent for using procedures to produce a multi-channeled structure such as that disclosed and claimed herein.

U.S. Pat. No. 4,965,245, issued Oct. 23, 1990 to Masaru Sugimoto et al. discloses a method of producing a superconducting cable or coil comprising a bundle of coated metallic filaments, for example, coated with an oxide, that are drawn and heated in oxidizing atmosphere to form a superconductor. Again, this patent neither discloses nor suggests a process for making channeled structures as disclosed and claimed herein.

SUMMARY OF THE INVENTION

In accordance with the present invention, a multi-channel structure comprising a body of structural material having a plurality of channels therein is produced by forming a composite rod comprising an outer shell formed of a powdered form of the structural material and a binder material and an inner core formed of a powdered form of a removable channel forming filler material and a binder material, assembling a first bundle of said composite rods in parallel relationship, consolidating said first bundle and reducing the diameter of the individual rods in said first bundle by deforming said first bundle, assembling a plurality of said deformed first bundles with a further bundle of said first bundles and consolidating the further bundle into a final assembly. The binder is then removed from both the outer shell material and the filler core material. The filler core material is removed and the resulting structure is sintered to produce the final structure containing channels as defined by the removed finer material of the cores of the respective composite rods of the final assembly of bundles. The binder and filler core material may be removed before sintering, during the sintering process or after sintering, for example, by evaporation, decomposition, dissolution, infiltration, melting with following blow out, etc.

In one embodiment, the structural material is a sinterable ceramic powder, such as alumina; the channel forming filler of the core is melamine or urea or a polymer, such as polyethylene or polypropylene; and the binder of both the core and outer shell is paraffin or wax.

Preferably, the viscosity or yield points of shell and core mixtures at extrusion temperature should be as close as possible to one another.

In the preferred embodiment, the binder is removed by heating. In this case, the binder should have a melting or boiling point below that of the filler core material. The filler core material can also be removed by heating, and this can be accomplished during the application of the heat used to preform the sintering step, which will require higher temperature than the melting or boiling point of the filler material.

In another embodiment, the structural material of the shell is formed of a powdered metal, such as tungsten or iron powders, and the channel forming filler material of the core is a low melting point metal powder, such as copper. In this embodiment, the binder has an essentially lower melting point than the core filler and may be paraffin or polyethylene or a mixture of several substances.

In another embodiment, the structural materials of the shell is formed of a metal alloy such as FeCrAlY or Hastealloys powders, and the channel forming filler material of the core is low carbon residue polymer such as melamine. In this embodiment, the binder may be wax and the filler and the binder materials may be removed partially or completely by organic solvent and/or by evaporation, before or during sintering.

In a further embodiment, the composite rod inner core is formed of at least one filler-binder rod formed of the channel forming filler material and the binder, and the outer shell is formed by positioning a plurality of rods formed of the mixture of structural and binder materials disposed around and parallel to the core to form a bundle which is deformed, for example, by extrusion to form the composite rod for practicing the method as described above.

OBJECTS AND ADVANTAGES OF THE INVENTION

It is an object of the present invention to provide a novel method using powdered materials for producing multi-channel structures comprised of materials such as ceramics, metals, intermetallics and polymers.

It is a further object to provide such method to produce multi-channel structures having relatively small diameter channels suitable for making structures usable as filters, catalyst carriers, heat exchangers, vents, etc.

The methods of the present invention enable the production of novel structures with channels that are of smaller diameter than those of prior methods and also with channels that are formed with relatively thin interchannel walls.

The novel methods of the present invention are simpler and less complex to perform than those of the prior art discussed above which requires the use of relatively expensive equipment including more complex dies, as compared to the simple single orifice dies that can be employed to practice the present invention, to produce structures with a plurality of channels of relatively small diameter.

This method can be used to produce porous polycapillary structures of different ceramics, intermetallics, and metals.

This technique allows control of the final porosity (from a few volume percent to 90 vol. % and more) channel diameter and interchannel wall thickness (from a few microns to a few millimeters) with small tolerance.

This technique can produce not only unidirectional channel structure, but can be adapted to produce bidirectional and three dimensionally porous structures as well.

DESCRIPTION OF THE PREFERRED EMBODIMENTS

Figure 1:
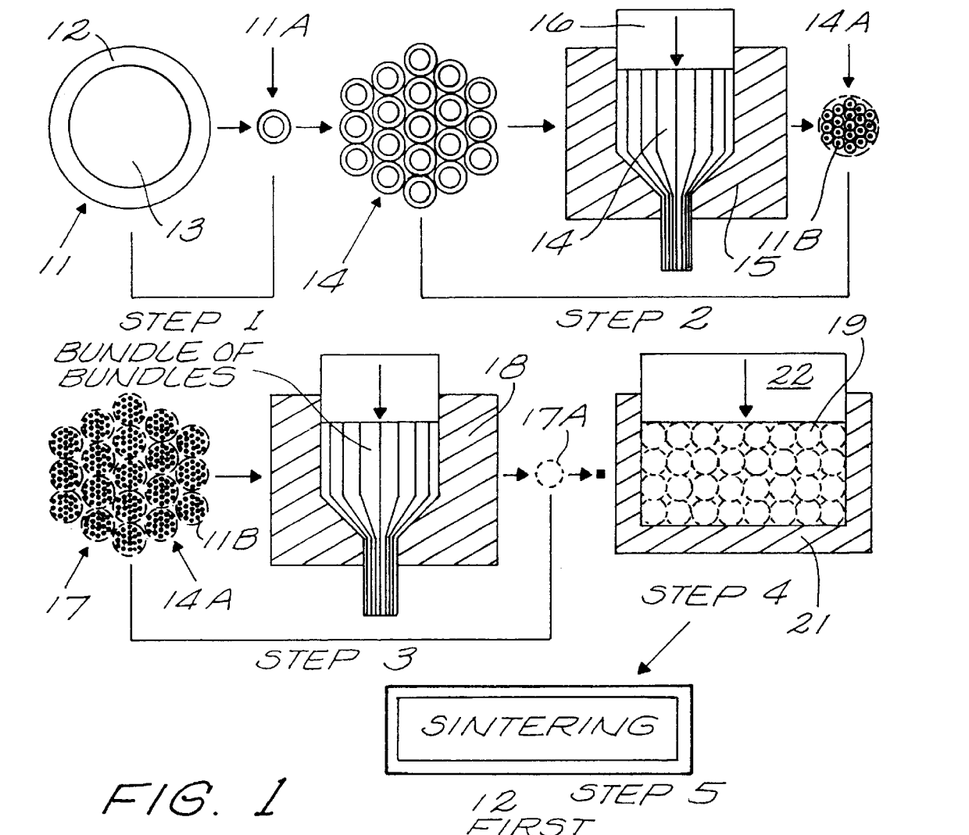
FIG. 1 is a schematic representation of the steps involved in producing a multi-channel structure according to the present invention.
Figures 2, 3:
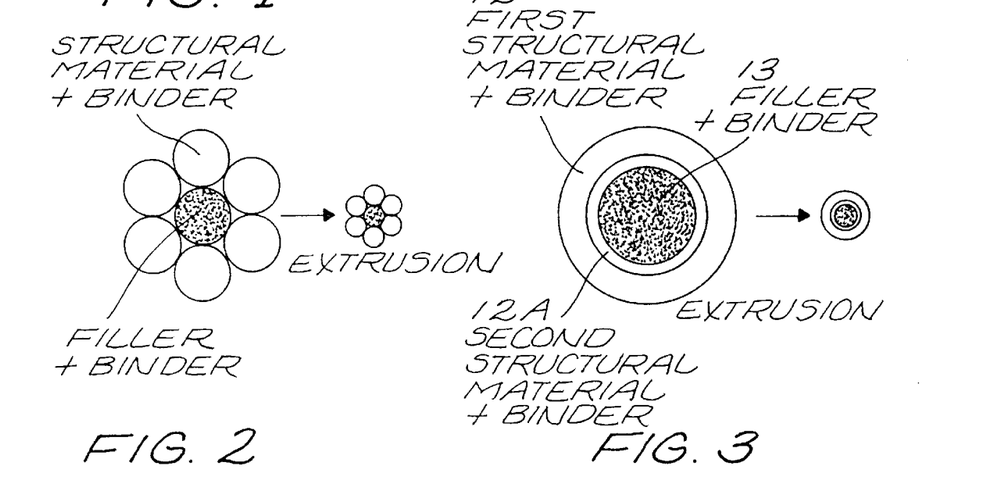
FIG. 2 is a schematic representation of a procedure comprising a cross sectional view of another embodiment of the composite rod shown in step 1 of FIG. 1.
FIG. 3 is a schematic representation of a cross sectional view of still another embodiment of the composite rod shown in step 1 of FIG. 1, wherein an additional layer comprised of a second structural matrix-binder mixture 12A is interposed between the outer structure matrix-binder layer 12 and the inner core 13.
Figure 4:
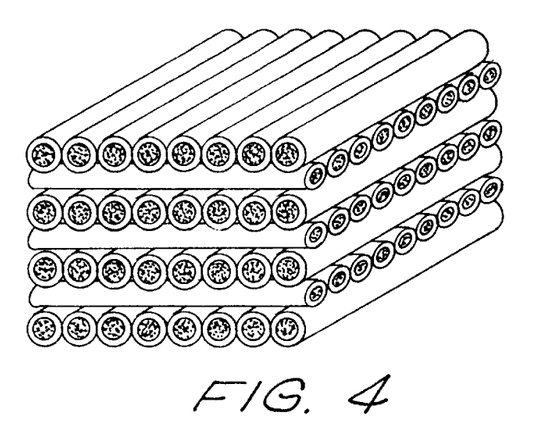
FIG. 4 is a schematic representation showing another embodiment of the final assembly of bundles 19 illustrated in step 4 of FIG. 1 for producing a structure with channels oriented in two perpendicular directions and having different diameters.
Figure 5A:
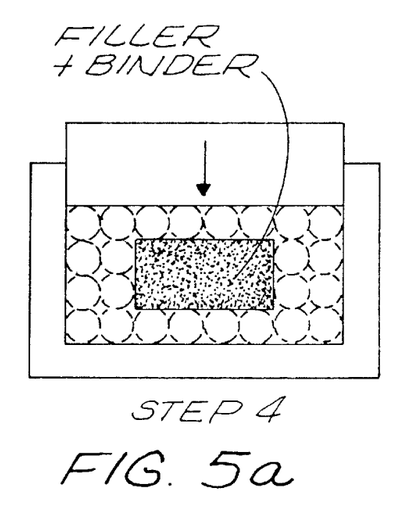
FIGS. 5a and 5b show the other embodiment of step 4 of FIG. 1 arranged to produce a large channel surrounded by multichannel structure (FIG. 5a) and to produce a solid central structure surrounded by multichannel structures (FIG. 5b)
Figure 5B:
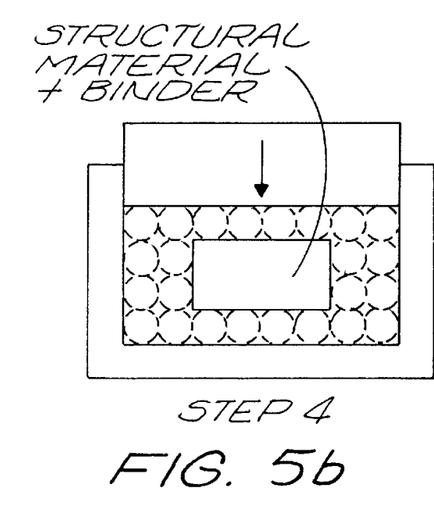

In FIG. 1, there is shown a cross-sectional view of a composite rod 11, comprising an outer shell 12 found of a first mixture comprised of a powdered form of a structural material such as alumina, and a binder material such as paraffin, and an inner core 13 formed of a second mixture comprised of a powdered form of a channel forming filler material such as melamine, and a binder such as paraffin.

The composite rod 11 may be formed, for example, by first producing a tube of the first mixture, for example by extrusion, to form the outer shell 12. The inner core 13 may be separately formed of the second mixture, for example by extrusion. The composite rod 11 may then be formed by inserting the inner core 13 into the shell 12.

Alternatively, the mixtures comprising the materials to form the outer shell 12 and the inner core 13 may simultaneously be extruded using a concentric two-channel die to form the composite rod 11.

Once the composite rod 11 is formed, as above, it can be further reduced in diameter, if desired, by extrusion to reduce its diameter to that illustrated as 11A in FIG. 1.

A bundle 14 of composite rods (11 or 11A) is then assembled as per step 2 illustrated in FIG. 1, wherein the composite rods shown as 11A are disposed parallel to one another, in cross section.

A convenient way of producing the several parallel rods (11A) is to produce a long composite rod (11) that may be cut into segments, either before or after reduction in diameter, to 11A, to form the various parallel rods to form the bundle 14.

The bundle 14 of assembled rods is then subjected to deformation, as by extrusion, per step 2 in an extruder 15, shown in cut-away side view, and which has an appropriately sized diameter die to deform and reduce the diameter of the bundle 14, to that shown as bundle 14A as well as the diameter of the individual composite rods 11A comprising the reduced diameter bundle 14A.

As per step 3 illustrated in FIG. 1, a further bundle 17 may be assembled of a plurality of parallel bundles 14A containing the further reduced diameter composite rods 11B. This further bundle 17 is then subjected to further deformation as per extruder 18, which is provided with a die of appropriate diameter to reduce further the diameter of the further bundle 17 to smaller diameter 17A, as shown per step 3. Of course, the extruder used in steps 1, 2 or 3 may be the same equipment, suitably provided with an extrusion die of the diameter desired for the respective step.

The procedure of assembling bundles of composite rods and deforming those bundles as by extrusion to reduce the diameter of the bundles as well as their constituent composite rods, thereby reducing the diameter of the individual cores 13 and increasing their number per given volume, can be carried out until the desired diameter and number of channel-forming cores is achieved.

The deformation of the assembled bundle of composite rods constitutes a consolidation of the numbers of the bundle, into a rod that may be of circular cross sectional configuration or rectangular or other form. However, it may be desirable to assemble the final bundle into a large assembly not easily consolidated by extrusion. In such case, the final assembly of bundles 17A may, for example, comprise a large bundle assembled in a die 21 for consolidation by compression within the die 21 by a plunger 22, per step 4.

The consolidated bundle 19 is then subjected to heat treatment per step 5, which includes removing the binder i.e. debinding, and removing the filler material as well as sintering of the remaining multi-channel green body structure comprised of the channeled structural material.

The selection of the filler, to a great degree, is dependent on the type of structural materials in that the filler should remain in place until sufficient mechanical integrity develops in structural material, but it should be removed under conditions that do not deteriorate the properties of the structural materials. In addition, the filler material should be chemically compatible with the structural material over the temperature range both in existence. Filler that remains to relatively high temperature before it is removed will have a wide range of applicability to a variety of structural materials. For example, MgO, CaO, etc. will not be removed during the process of sintering, they allow for the holding of the shape of the channels during sintering, and they can be removed by dissolution after sintering. Accordingly, they could be used as fillers for high temperature refractory metals such as W, Ta, and the like, when the development of sufficient structural integrity of the shell require temperatures as high as 800° to 1200° C. Clearly, filler material should not form new undesirable compounds with the structural material. If low temperature polymer is used which is removed before structural materials develop sufficient mechanical integrity, the multi-channel structure could be unstable and collapse. It is possible to use lower melting temperature filler, but in that case, the filler removal should be conducted very slowly in the powder bed to support the structure.

The chemical composition of the channeled structural materials will typically be that of the starting structural powder materials used to form the composite rods. However, desired chemical composition of structure materials can also be obtained by starting with mixed structural powders and causing the powder to react during or after sintering to form the desired composition. For example, metal alloys such as FeCrAlY, which is a high temperature alloy with high room temperature ductility and exceptional cyclic oxidation resistances and excellent shock resistance which are properties that make this alloy an excellent catalyst support for high temperature applications, can be made from the corresponding alloy powders or by mixing at the appropriate stoichiometric ratio the corresponding elemental metal powdered components of the alloys, and forming the alloy in-situ during or after sintering by applying heat to cause the elemental metal component to form the desired alloy. When the FeCrAlY multi-channel structure is formed, catalyst such as platinum can be applied by dip coating or electrodeposition to form the catalyst product for such applications as catalytic converters. Furthermore, the catalyst such as platinum can be incorporated as one of the powdered components of the structural material that is used to form the composite rods. The same methods can be applied to form desired intermetallics such as nickel aluminide from nickel and aluminum powders. Likewise this method can be used to form ceramic compositions such as silicon carbide from silicon and carbon powders in multi-channel structural material. This technique allows for starting with less costly raw materials with the desired properties such as particle size.

The process consists of the following steps (FIG. 1):

Step 1—Production of bi-material rods, 11, consisting, for example, of shell (alumina+binder) and core (filler+binder). The shell comprises a mixture of alumina powder with a binder additive (wax, parafin, or some thermoplastic polymer like ethylene vinyl acetate, ethylene ethyl acrylate, etc.). The core comprises a mixture of the binder with a powder of channel-forming filler which can be removed afterwards by evaporation, melting, dissolution, etc. The powders of organic like urea, melamine, polymers) or inorganic (like CaO, MgO, metals) substances can be used as the fillers. The desirable rods with diameters in the range of 0.1–10 mm will be produced by extrusion of larger diameter (20–200 mm) bi-material rods 11.

Step 2—Assembling the rods into a bundle and re-extruding the bundle: As a result of this step, a green composite blank (rod) that comprises of matrix (alumina+binder) and channel-forming fibers (filler+binder) will be obtained. However, the fibers produced by this stage of extrusion may still have too large a diameter—up to a few hundred microns, hence further reduction in scale may be necessary.

Step 3—Repeating step 2 for further refinement in scale of channels: At the conclusion of this step, the rods obtained will have diameters of 0.1–10 mm, with channel-forming fibers of a diameter of 10–100 microns, depending on the extrusion ratio. This step can be repeated, if necessary, to get even smaller diameter fibers.

Step 4—Assembling the rods produced in step 3 into a bundle and their consolidation in a die, or by cold isostatic pressing, cold extrusion, cold rolling, etc., in order to get the desired green density prior to hot-densification.

Step 5—Densification. This step includes sequentially (1) removing the binder, (2) removing the filler, and (3) sintering the multi-channel alumina green body. The sintering occurs in such a manner that thermally-induced cracks are avoided and provides high density of the interchannel walls in order to get high strength of filter. If paraffin is used as binder, its removal will occur at 150°–350° C. To remove urea or melamine filler, temperatures of about 300°–500° C. are required. Sintering of alumina will occur at 1500°–1700° C.

By engineering such a multi-channel product through design and control of the microstructure, a variety of ceramic metallic or intermetallic products with properties that are tailored to desired end use can be produced. For example, if product with channel diameter 20 micrometers is required, at stage 1 a bi-material rod with core diameter 0.5 mm and shell diameter 1 mm can be obtained. Then, on the stage 2, a bundle of 1000 of these rods should be collected and extruded from diameter 36 mm to diameter 1 mm, so after stage 2, we will have a diameter of fibers from filler+binder mixture (and hence future channels) in this rod of ~20 micrometers. Step 3 in this case can be excluded. Rods obtained in step 2 should be bundled, pressed (step 4), and sintered (step 5). If smaller diameter channels are required, step 3 may be reincluded.

Thus, the method of this invention is to use repeated coextrusion of a rod structure comprised of a removable inner core comprised of a mixture of filler and binder powders and an outer shell comprised of a mixture of binder powder and of sinterable structural powder material to form a fiber reinforced ceramic matrix green blank to be followed by debinding, removal of the fibers found by the filler material and sintering of the matrix. In this way, multichannel structures with controlled diameters and distribution of straight microchannels are formed.

EXAMPLES

Example 1

Step 1—a first mixture of 85 weight % alumina powder (aver. particles diameter 1.3 $\mu$m) and 15 wt % paraffin, a binder, was prepared. This first mixture was heated at 90° C. and blended.

Step 2—a second mixture of 79 wt % melamine powder (aver. particle size 2.5 $\mu$k) and 21 wt % paraffin binder was prepared like the mixture in step 1.

Step 3—The two mixtures prepared in step 1 and step 2 were loaded in the 2-channel extruder and extruded at 45° C. As a result, bi-material rods, having a core of 1 mm in diameter and sheath 2 mm in diameter were produced. The core consisted of the second mixture of melamine powder with paraffin and the sheath consisted of the first mixture of alumina powder with paraffin.

Step 4—The bi-material rods obtained in step 3 were cut into 100 mm segments, and a bundle of 631 such segments was assembled, and the bundle, which was in substantially parallel relationship was inserted into the die, which had a container 90 mm in diameter and outgoing hole 3 mm in diameter, and extruded. As a result, the rod 3 mm in diameter was produced that had the structure of fiber reinforced composite with matrix of mixture alumina powder and paraffin binder and with 631 fibers comprised of mixture of melamine powder with paraffin binder. The diameter of each fiber was approximately 60 micrometers.

Step 5—The bundles of rods obtained in step 4 were cut into 50 mm length segments and 300 such segments were stacked in parallel relationship into a rectangular 50×90 mm die (10 layers, each layer of 30 segments), then the stack was pressed at 40° C. (pressure 1500 N/cm$^2$) in order to consolidate the stack of rods. As a result, the rectangular green (i.e., uncured) composite structure having 189300 fibers was obtained.

Step 6—The green body structure obtained in step 5 was heated and sintered. The procedure of the heat treatment was as follows:

heating while raising the temperature from 20° C. to 250° C. at a rate of 5° C./hour, hold the upper temperature for 0.5 h, then continue heating while raising the temperature to 350° C. at a rate of 15° C./h, hold the upper temperature for 1 h, then continue heating while raising the temperature to 540° C./h, hold for 1 hr, heating to 815° C. with rate 100° C./h, hold 1 h, heating to 1090° C. at a rate 100° C./h, and hold 1 h. As a result, the rectangular multi-channel sintered alumina product having 189300 continuous parallel ducts ~40 micrometers in diameter was obtained.

Example 2

Step 1—Bi-material rods, consisting of the 1 mm outer diameter shell, which comprises a first mixture of tungsten powder (average size of particles—5 micrometers) with 48 vol % binder (34% paraffin wax, 33% polyethylene wax and 33% beeswax) and of the 2.5 mm diameter core comprises a second mixture of 5 micrometers copper powder with 60 vol % of the same binder were produced by extrusion of 60 mm diameter bi-material green body into diameter 4 mm.

Step 2—169 bi-material rods, obtained in step 1, were assembled in substantially parallel relationship into a bundle, which was inserted into 60 mm barrel and extruded through a 2 mm diameter die. As a result of this step, a bundle of 2 mm diameter green composite rods comprised of (W+binder) matrix and 169 (Cu+binder) fibers, having diameter ~0.1 mm were obtained.

Step 3—The bundles of 2 mm rods, produced in the step 3, were cut into segments 50 mm length, these bundles of segments were placed in the square die 50×50 mm, and pressed with a force of 6000 kgf in order to consolidate the assembled rods.

Step 4—The green body (i.e., uncured structure), obtained after step 3 was heated in H$_2$ atmosphere from 20° C. to 500° C. at the rate of 0.2° C./min. for the binder removal, then heated in a hydrogen atmosphere at temperatures ranging from 500° C. to 1280° C. with a rate of 5° C./min. In the process of heating, Cu starts to melt at 1083° C., infiltrates the W matrix and leaves channels instead of fibers. The interchannel walls that comprise the resulting structure consist of W-Cu pseudoalloy.

Example 3

Step 1—Bi-material rods, consisting of the 1 mm outer diameter shell, which is comprised of a first mixture of carbonyl Fe powders with 40 vol % binder (85% paraffin and 15% beeswax), and of the 0.81 mm diameter core comprised of a mixture of melamine powder with 50 vol % the same binder, were produced by extrusion of 60 mm diameter bi-material green body (54 mm diameter core of melamine with binder and 60 mm diameter shell of Fe with binder) into diameter 1 mm.

Step 2—The rods obtained in step 1 were cut to segments 100 mm length and a bundle of 1027 bi-material segments was assembled into a bundle of parallel rods which was isopressed at 45° C. at pressure 10 MPa in order to consolidate the assembled rods.

Step 3—The green body $\phi$30 mm obtained after step 2 was heated in an atmosphere of H$_2$ with temperature raised from 20° C. to 500° C. at a rate of 0.2° C./min. in order to remove the binder and melamine, then sintered by being heated in an atmosphere of H$_2$ from a temperature raised from 500° C. to 1200° C. at a rate of 5° C./min and held at 1200° C. for two hours. As a result, after sintering, the resulting structure of iron comprising a rod ~87 mm length and 25 mm diameter with 1027 channels of 0.66 mm diameter was produced.

Example 4

Step 1—A first mixture of 63 vol % alumina powder (aver. particle size ~1.3 μm) and 37 vol % binder (80% paraffin+20% polyethylene) was prepared.

Step 2—A second mixture of 60 vol % magnesia powder (aver. particle size ~1.8 μm) and 40 vol % binder (80% paraffin+20% polyethylene) was prepared.

Step 3—The 2 mixtures prepared in steps 1 and 2 were loaded in the two-channel extruder with the first mixture arranged to be extruded as the outer shell over the first mixture as an inner core and extruded at 55° C. As a result, bi-material rods having core 2 mm in diameter and shell 4 mm in diameter, were produced. The cores consisted of the second mixture (magnesia+binder) and the shell consisted of the first mixture (alumina+binder).

Step 4—Bi-material rods obtained in step 3 were bundled, inserted into the die which had a container 90 mm in diameter and outgoing hold 20 mm in diameter, and extruded. As a result, the 20 mm diameter green body rod structure with 91 future channels was produced.

Step 5—The green body structure obtained in step 5 was heated and sintered. The procedure of the heat treatment was as follows:
heating from 20° C. to 500° C. at a rate of 5° C./hr, then heating from 500° C. to 1100° C. at a rate of 60° C./hour, holding the upper temperature for 1 hour, then heating with a rate of 30° C./hour from 1100° C. to 1500° C., holding 1 hour.

Step 6—A piece of the sintered structure obtained in the step 5 was cut into segments 20 mm in length, the segments were placed into $HNO_3$ at 60° C. and held there for 6 hours. MgO fibers were dissolved from the structure and left channels ~1 mm in diameter in the remaining structure.

Example 5

To produce an alumina multi-channel structure, alumina powder with 1.3 μm particle size were mixed with 50 vol % binder (paraffin wax/beeswax) to give a viscous mixture at ~45°–50° C. In the next step, this mixture was extruded through a 12 mm die, connected to a 60 mm container. As a result, a 12 mm rod was produced out of alumina-binder mixture and cut into smaller pieces (~100 mm each).

Using the same technique, the filler-binder mixture was prepared out of melamine powder (50 vol %) and a binder (paraffin wax/beeswax) and this filler-binder mixture was extruded into the same sized 12 mm rods.

In the next step, the rods of alumina-binder and filler-binder were arranged into a bundle with one filler-binder rod in the middle and two concentric layers around it—the first layer comprising filler-binder rods and the second (external) layer comprising alumina-binder rods. After extrusion of this bundle through the same 12 mm die, a green body structure formed of bi-material rods was obtained with an alumina-binder shell and filler-binder in the middle. In the next step, the rods were cut into 100 mm pieces which were assembled in a bundle of parallel rods and loaded into the 60 mm container for re-extrusion through a 12 mm die again. As a result of this step, a rod assembly comprising an alumina-binder matrix and 19 filled passages with the filler-binder matrix was obtained.

After cutting into smaller pieces, the green body structure comprised of a bundle of 12 mm rods with 19 filled passages—was embedded into fine alumina powder and heat treated in the air. The alumina powder removes the liquefied binder by capillary action during the heat treatment which caused the wax binder to melt. The de-binding process was conducted with 5°–6° C./hr. heating rate, 2 hr. hold time, then heating the sample up to 1100° C. with 30°–35° C./hr heating rage, 2 hr. hold time and cooling down with the furnace. After the sample was removed from the embedding powder, it was further sintered at 1400° C. with slow heating rate and 2 hr. hold time. Note that we have also used carbon powder in place of the Alumina powder to absorb the liquefied binder.

As a result, an alumina structure sample comprising 19 channels was produced. The OD after sintering was 9.3 mm and the channel size ~1.6 mm with the volume fracture of channels of about 69% and 1 mm wall thickness between the channels.

Example 6

To produce a multi-channel structure formed of Zirconia stabilized with Yittria, Zirconia powder stabilized with Yittria was used. Particle size was in the range of 1–5 μm. The stabilized Zirconia powder was mixed with 55 vol % binder (paraffin wax/beeswax) at 55°–60° C. to produce viscous homogeneous substance. Using the same technique as described in Example 5, two kinds of 12 mm rods—one formed of "$ZrO_2/Y_2O_3$—Binder" and the other formed of "filler-binder" as in example 5 were fabricated and jointly re-extruded (at 570° C.) to produce 12 mm bi-material rods—with a shell comprising of $ZrO_2/Y_2O_3$ and a core comprising the filler-binder materials. In the next step, the bi-material rods were cut into 19 pieces and arranged in a bundle consisting of one filler-binder rod in the center and two concentric layers around with 6 and 12 rods in them, respectively. The first concentric layer was comprised of filler-binder rods and the second (external) layer was comprised of $ZrO_2/Y_2O_3$-binder rods. The bundle was inserted into a 60 mm container and extruded through a 12 mm die to produce a rod structure comprising a $ZrO_2/Y_2O_3$ matrix and 19 2.4 mm passages filled with the filler matrix. On the next step, the produced rod structure was cut into 19 more pieces and re-extruded as described above to produce 12 mm rod with $ZrO_2/Y_2O_3$ matrix and 19×19=361 passages (~0.45 mm in dia) filled with filler material matrix.

After cutting to a required length, these rod structures were subjected to a similar heat treating process as described in Example 5 with final sintering at 1500° C.

As a result, a $ZrO_2/Y_2O_3$ structure comprising 361 channels was produced. The OD after sintering was reduced to about 9.8 mm and the channel size—to about 0.3 mm with wall thickness of 0.25 mm giving total channel porosity of 58%.

Example 7

The high temperature metal alloy, (FeCrAlY) multi-channel rod with 85% volume loading of channels and channel diameter of ~0.5 mm was produced in the following manner:

Powder of Fe-25Cr-5Al-0.5Y was mixed with 45 vol % binder paraffin wax/beeswax), the mixture was extruded through a 5 mm die and the obtained rod was cut into segments 100 mm long and 5 mm diameter.

Using the same technique, the filler-binder mixture was prepared out of melamine powder (50 vol %) and a binder (paraffin wax/beeswax). After extrusion, the rod of this filler-binder mixture of diameter 55 mm was obtained.

The parallel rods of FeCrAlY-binder and filler-binder were arranged into a parallel bundle with one filler-binder rod in the middle and one concentric external layer comprising fecralloy-binder rods around it. After extrusion of this bundle through the 0.75 mm die at 45° C., a bi-material rod was obtained with an FeCrAlY-binder shell and filler-binder in the middle. On the next step, the rod was cut into 40 mm segments long which were assembled in a bundle of 1000 parallel segments, the bundle was loaded into the die of rectangular cross-section 40×30 mm and compacted under pressure 15 MPa at temperature 45° C. As a result of this step, a green body 40×30×12 mm comprising a FeCrAlY-binder matrix with 1000 uniformly distributed parallel filler-binder fibers was obtained. Debinding and sintering was carried out to remove binder and filler and as a result, the preassigned multi-channel FeCrAlY structure with 1000 channels oriented perpendicular to the plane 40×12 mm is obtained.

The debinding was carried out by slow heat (0.1° C./minute) to 350° C. followed by holding for 10 hours, and the sintering was carried out by heating from 350° C. to 1400° C. at a rate of 0.2° C./min in an ultrapure hydrogen atmosphere, with 2 hours holding at 1400° C.

Example 8

In much the same way as is described in the previous example, the 40×30×12 mm multi-channel green bar of superalloy Hastelloy X was manufactured. It had 85% volume fraction of channels of 0.5 mm diameter. The powdered mixture Ni-45%, Cr-22%, Fe-18%, Mo-9%, Co-1.5%, W-0.5% was used as the structural material. It was mixed with the 50 vol % of binder comprising 85% paraffin and 15% beeswax and the mixture obtained was used as shell of bi-material rod. The core of the rod was made of a mixture of 55% melamine+50% the same binder. Procedure of manufacturing green body was the same as in the Example 8.

REFERENCES

1. Y. Zheng, S. Sridar, and K. C. Russel, "Controlled Porosity Alloys Through Solidification Processing: A Modelling Study," *Materials Research Society Symposium Proceedings, Vol. 371, Advances in Porous Materials,* December, 1994, p. 365–370.
2. A. Pattnaik, S. C. Sanday, C. L. Vold and H. I. Aaronson, "Microstructure of Gasar Porous Ingot," *Materials Research Society Symposium Proceedings, Vol. 371, Advances in Porous Materials,* December, 1994, p. 371–376T.
3. J. M. Wolla and V. Provenzano, "Mechanical Properties of Gasar Porous Copper," *Materials Research Society Symposium Proceedings, Vol. 371, Advances in Porous Materials,* December, 1994, p. 377–382.

I claim:

1. A method of producing a solid multi-channeled structure formed of a structural material having a plurality of channels therein comprising the steps of:
   a. providing a first mixture comprised of a powdered form of said structural material and a binder material;
   b. providing a second mixture comprised of a powdered form of a channel forming filler material and a binder material;
   c. forming a composite rod comprising an outer shell formed of said first mixture and an inner core formed of said second mixture by deforming said second mixture to form said core and deforming said first mixture to form said outer shell surrounding said core;
   d. assembling a first bundle comprising a plurality of said composite rods in substantially parallel relationship with one another and consolidating said first bundle and reducing the diameter of the individual rods in said first bundle by deforming said bundle;
   e. assembling a plurality of said deformed bundles into a further bundle comprising a final assembly in the form of the desired structural configuration;
   f. consolidating the further bundle comprising said final assembly while maintaining the filler and binder of the composite rods of said assembly in place;
   g. then, removing the binder from both the core material and the shell material of the composite rods comprising the consolidated final assembly;
   h. then, sintering the resulting structure comprising the remaining structural material of the outer shells of the composite rods of the final assembly, and, removing the channel-forming filler material from the inner core of the composite rods comprising the consolidated final assembly; thereby producing a solid structure having a plurality of channels therein as defined by the removed filler material forming the cores of the composite rods comprising the final assembly structure.

2. The method of claim 1, wherein the removal of the channel-forming filler material per step (h) is accomplished by the sintering step (h).

3. The method of claim 1, wherein the removal of the channel-forming filler material per step (h) is accomplished, by step (i) that is separate from the sintering step (h).

4. The method of claim 1, wherein the diameter of the individual rods of said first bundle of composite rods, after deforming said bundle per step (d), is further reduced prior to being incorporated in said final assembly of step (e) by at least one additional step of deformation in a further bundle comprised of parallel bundles of deformed bundles of reduced diameters.

5. The method of claim 1 wherein the composite rod is formed by deformation of said first and second mixtures per step (c) by extruding said second mixture through an inner orifice and extruding said first mixture through an outer annular orifice to form said outer shell surrounding said core.

6. The method of claim 4 wherein the composite rod is formed by deformation of said first and second mixtures per step (c) by extruding said second mixture through an inner orifice and extruding said first mixture through an outer annular orifice to form said outer shell surrounding said core.

7. The method of claim 1 wherein the step (d) of reducing the diameter of the individual rods in said first bundle by deforming said bundle involves extruding said bundle through an orifice that is smaller than the original circumference of said first bundle.

8. The method of claim 5 wherein the step (d) of reducing the diameter of the individual rods in said first bundle by deforming said bundle through an orifice that is smaller than the original circumference of said first bundle.

9. The method of claim 4 wherein the additional deformation of said bundle of rods to reduce the diameter of the individual rods involves extrusion of said further bundle of rods.

10. The method of claim 8 wherein the additional deformation of said bundle of rods to reduce the diameter of the individual rods involves extrusion of said further bundle of rods.

11. The method of claim 1 wherein the binder material of said first mixture and the binder material of said second mixture are comprised of thermoplastic material.

12. The method of claim 4 wherein the binder material of said first mixture and the binder material of said second mixture are thermoplastic.

13. The method of claim 11 wherein the channel forming material of said second mixture is thermoplastic material having a melting point above the melting point of that of the binder material of both the first and second mixtures.

14. The method of claim 12 wherein the channel forming material of said second mixture is thermoplastic material having a melting point above the melting point of that of the binder material of both the first and second mixtures.

15. The method of claim 1, wherein the channel-forming material of the second mixture is material having a boiling point above the boiling point of that of the binder material.

16. The method of claim 1 wherein the structural material of said first mixture is a sinterable ceramic powder.

17. The method of claim 4 wherein the structural material of said first mixture is a sinterable ceramic powder.

18. The method of claim 11 wherein the structural material of said first mixture is a sinterable ceramic powder.

19. The method of claim 12 wherein the structural material of said first mixture is a sinterable ceramic powder.

20. The method of claim 13 wherein the structural material of said first mixture is a sinterable ceramic powder.

21. The method of claim 14 wherein the structural material of said first mixture is a sinterable ceramic powder.

22. The method of claim 15 wherein the ceramic powder structural material of said first mixture is alumina.

23. The method of claim 17 wherein the ceramic powder structural material of said first mixture is alumina.

24. The method of claim 18 wherein the ceramic powder structural material of said first mixture is alumina.

25. The method of claim 19 wherein the ceramic powder structural material of said first mixture is alumina.

26. The method of claim 20 wherein the ceramic powder structural material of said first mixture is alumina.

27. The method of claim 21 wherein the ceramic powder structural material of said first mixture is alumina.

28. The method of claim 11, wherein the channel-forming filler of said second mixture is a substance selected from among urea, melamine and a polymer.

29. The method of claim 1, wherein the vaporization temperature of the channel-forming filler material is lower than the sintering temperature of the structural material of said first mixture.

30. The method of claim 12, wherein the channel-forming filler of said second mixture is a substance selected from among urea, melamine and a polymer.

31. The method of claim 11 wherein the channel-forming filler of said second mixture is a substance selected from among carbonaceous materials, CaO, MgO and metal.

32. The method of claim 12, wherein the channel-forming filler of said second mixture is a substance selected from among carbonaceous materials, CaO, MgO and metal.

33. The method of claim 31, wherein the binder of said first mixture is wax or paraffin.

34. The method of claim 32 wherein the binder of said first mixture is wax or paraffin.

35. The method of claim 33, wherein the binder of said second mixture is also wax or paraffin.

36. The method of claim 1, wherein the step (e) of assembling the extruded bundles into the final assembly involves positioning the respective bundles in layers that are substantially parallel to one another, whereby the resulting solid structure of the sintering step (h) contains a plurality of parallel channels in layers that are in substantially parallel relationship, contains a plurality of parallel channels from one side of the structure to another.

37. The method of claim 4, wherein the step (e) of assembling the extruded bundles into the final assembly involves positioning the respective bundles in parallel relationships, whereby the resulting solid structure of the sintering step (h) contains plurality of parallel channels from one side of the structure to another.

38. The method of claim 5, wherein the step (e) of assembling the extruded bundles into the final assembly involves positioning the respective bundles in layers that are substantially parallel to one another, whereby the resulting solid structure of the sintering step (h) contains a plurality of parallel channels in layers that are substantially parallel from one side of the structure to another.

39. The method of claim 1, wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

40. The method of claim 4, wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

41. The method of claim 5, wherein the step (e) of assembling the extruded bundles into the final assembly involves positioning the respective bundles in layers that are alternately transverse to one another, whereby the resulting solid structure of the sintering step (h) contains a plurality of parallel channels in layers that are alternately transverse to one another.

42. Solid multi-channel structure produced by the method of claim 36.

43. Solid multi-channel structure produced by the method of claim 37.

44. Solid multi-channel structure produced by the method of claim 38.

45. Solid multi-channel structure produced by the method of claim 39.

46. Solid multi-channel structure produced by the method of claim 40.

47. Solid multi-channel structure produced by the method of claim 41.

48. A solid multi-channel structure produced by the method of claim 42, wherein the channels of the final assembly have a diameter in the range of 10–100 microns.

49. A solid multi-channel structure produced by the method of claim 43, wherein the channels of the final assembly have a diameter in the range of 10–100 microns.

50. A solid multi-channel structure produced by the method of claim 44, wherein the channels of the final assembly have a diameter in the range of 10–100 microns.

51. A solid multi-channel structure produced by the method of claim 45, wherein the channels of the final assembly have a diameter in the range of 10–100 microns.

52. A solid multi-channel structure produced by the method of claim 46, wherein the channels of the final assembly have a diameter in the range of 10–100 microns.

53. A solid multi-channel structure produced by the method of claim 47, wherein the channels of the final assembly have a diameter in the range of 10–100 microns.

54. The method of claim 11, wherein the binder material of said first and second mixtures is paraffin, the filler material is urea or melamine, wherein the step of removing the binder from the core and shell materials of the consolidated final assembly involves subjecting the consolidated final assembly to heat in the range of 150° C.–350° C., and wherein the step (I) of removing the filler material from the consolidated final assembly involves subjecting the consolidated final assembly to heat in the range of 300° C.–500° C., and wherein the curing step (I) involves sintering by subjecting the remaining structures of the final assembly to heat in the range of 1500° C.–1800° C.

55. The method of claim 1 wherein the metal powder structural material of said first mixture consists essentially of powdered metal.

56. The method of claim 4, wherein the metal powder structural material of said first mixtures consists essentially of powdered metal.

57. The method of claim 5 wherein the metal powder structural material of said first mixture consists essentially of powdered metal.

58. The method of claim 55, wherein the channel forming filler material of said second mixture consists essentially of another powdered metal having a lower melting point than that of the powdered metal structural material of said first mixture.

59. The method of claim 57, wherein the channel-forming filler material of said second mixture consists essentially of another powdered material having a lower melting point than that of the powdered metal structural material of said first mixture.

60. The method of claim 57, wherein the channel-forming filler material of said second mixture consists essentially of another powdered metal having a lower melting point than that of the powdered metal structural material of said first mixture.

61. The method of claim 58 wherein the step (h) of claim 1 of removing the channel-forming filler material from the inner core of the composite rods of the final assembly involves subjecting said consolidated final assembly to heat at a temperature sufficiently high to melt the powdered metal binder core material of said assembled rods but not high enough to melt the structural material forming the outer shells of said assembled rods and wherein the melted metal binder material infiltrates the matrix comprising the metal of the outer shells of the assembled rods, thereby providing channels in the final assembly in place of the melted core material.

62. The method of claim 58, wherein the step (h) of claim 1 of removing the channel-forming filler material from the inner core of the composite rods of the final assembly involves subjecting said consolidated final assembly to heat at a temperature sufficiently high to melt the powdered metal binder core material of said assembled rods but not high enough to melt the structural material forming the outer shells of said assembled rods, and wherein the melted metal binder material infiltrates the matrix comprising the metal of the outer shells of the assembled rods, thereby providing channels in the final assembly in place of the melted core material.

63. The method of claim 59, wherein the step (h) of claim 1 of removing the channel-forming filler material from the inner core of the composite rods of the final assembly involves subjecting said consolidated final assembly to heat at a temperature sufficiently high to melt the powdered metal binder core material of said assembled rods but not high enough to melt the structural material forming the outer shells of said assembled rods and wherein the melted metal binder material infiltrates the matrix comprising the metal of the outer shells of the assembled rods, thereby providing channels in the final assembly in place of the melted core material.

64. The method of claim 58 wherein the powdered metal structural material of the first mixture consists essentially of Tungsten.

65. The method of claim 64, wherein the powdered metal channel forming filler material consists essentially of copper.

66. The method of claim 59 wherein the powdered metal structural material of the first mixture consists essentially of Tungsten.

67. The method of claim 66, wherein the powdered metal channel forming filler material consists essentially of copper.

68. The method of claim 58, wherein the powdered metal structural material of the first mixture consists essentially of Tungsten.

69. The method of claim 68, wherein the powdered metal channel-forming filler material consists essentially of copper.

70. The method of claim 55 wherein the channel forming filler material of said second mixture consists essentially of an organic substance.

71. The method of claim 70, wherein the organic substance is melamine powder.

72. The method of claim 56 wherein the channel-forming filler material of said second mixture consists essentially of an organic substance.

73. The method of claim 72 wherein the organic substance is melamine powder.

74. The method of claim 57 wherein the channel-forming filler material of said second mixture consists essentially of an organic substance.

75. The method of claim 74 wherein the organic substance is melamine powder.

76. The method of claim 55 wherein the powdered metal of said first mixture consists essentially of powdered carbonyl iron.

77. The method of claim 56 wherein the powdered metal of said first mixture consists essentially of powdered carbonyl iron.

78. The method of claim 57 wherein the powdered metal of said first mixture consists essentially of powdered carbonyl iron.

79. The method of claim 75, wherein the powdered metal of said first mixture consists essentially of powdered carbonyl iron.

80. The method of claim 71, wherein the powdered metal of said first mixture consists essentially of powdered carbonyl iron.

81. The method of claim 77 wherein the powdered metal of said first mixture consists essentially of powdered carbonyl iron.

82. The method of claim 62, wherein the powdered metal of said first mixture consists essentially of powdered carbonyl iron.

83. The method of claim 63, wherein the powdered metal of said first mixture consists essentially of powdered carbonyl iron.

84. The method of claim 64, wherein the powdered metal of said first mixture consists essentially of powdered carbonyl iron.

85. Solid multi-channel structure produced by the method of claim 34.

86. Solid multi-channel structure produced by the method of claim 21.

87. Solid multi-channel structure produced by the method of claim 22.

88. Solid multi-channel structure produced by the method of claim 28.

89. Solid multi-channel structure produced by the method of claim 31.

90. Solid multi-channel structure produced by the method of claim 35.

91. Solid multi-channel structure produced by the method of claim 1.

92. Solid multi-channel structure produced by the method of claim 2.

93. Solid multi-channel structure produced by the method of claim 3.

94. Solid multi-channel structure produced by the method of claim 4.

95. Solid multi-channel structure produced by the method of claim 69.

96. Solid multi-channel structure produced by the method of claim 84.

97. A solid multi-channel structure as defined by claim 85, wherein the channels of the final assembly have a diameter in the range of 10–100 microns.

98. A solid multi-channel structure as defined by claim 86, wherein the channels of the final assembly have a diameter in the range of 10–100 microns.

99. A solid multi-channel structure as defined by claim 87, wherein the channels of the final assembly have a diameter in the range of 10–100 microns.

100. A solid multi-channel structure as defined by claim 88, wherein the channels of the final assembly have a diameter in the range of 10–100 microns.

101. The solid multi-channel structure of claim 91, wherein the channels of the final assembly have a diameter in the range of 10–100 microns.

102. The solid multi-channel structure of claim 94, wherein the channels of the final assembly have a diameter in the range of 10–100 microns.

103. The method of claim 51, wherein the first mixture containing the powdered form of said structural material comprises a catalyst.

104. The method of claim 55, wherein the first mixture containing the powdered form of said structural material comprises a catalyst.

105. The method of claim 1, wherein the channel-forming filler material is acid soluble, the structural material is acid insoluble, and the filler material is selectively removed per step (h) by subjecting it to an acid solution.

106. The method of claim 105, wherein the channel-forming filler material is an acid soluble metal and the structural material is alumina.

107. The method of claim 106 wherein the channel-forming filler material is copper.

108. The method of claim 106 wherein the channel-forming filler material is iron.

109. The method of claim 107 wherein the acid is hydrogen chloride.

110. The method of claim 108 wherein the acid is sulfuric.

111. The method of claim 1, wherein the step (c) of forming a composite rod comprising an outer shell formed said first mixture and an inner core formed of said second mixture involves the preliminary steps of:

(i) forming a plurality of structure-binder rods comprised of said first mixture;

(ii) forming at least one filler-binder rod comprised of said second mixture; and (iii) forming the composite rod of step (c) of claim 1 by assembling a bundle of parallel rods wherein the core is comprised of at least one of said filler-binder rods and the outer shell is comprised of a plurality of said structure-binder rods disposed around the core and wherein the assembled bundle of the parallel rods is deformed per step (c) to form the composite rod.

112. The method of claim 111, wherein the composite rod of step (c)(iii) is formed by deforming the assembled bundle of parallel rods by extrusion.

113. The method of claim 111, wherein the structural material of said first mixture is a sinterable ceramic powder.

114. The method of claim 113, wherein the sinterable ceramic powder is alumina.

115. The method of claim 114 wherein the channel-forming filler material of said second mixture is a substance selected from among melamine and a polymer.

116. The method of claim 113, wherein the sinterable ceramic powder is Zirconia powder stabilized with Yttria.

117. The method of claim 116, wherein the channel-forming filler material of said second mixture is a substance selected from among melamine and a polymer.

118. The method of claim 111 wherein the composite rod formed per step (c) comprises an intermediate layer between the outer shell and the inner core and which is comprised of a third mixture consisting of a powdered form of a second structural material and a binder material and which involves the additional preliminary steps of (iv) forming a plurality of rods of said catalyst-binder material, (v) assembling a plurality of said second structural material-binder rods in said bundle of parallel rods disposed parallel to and between the core and the structure-binder rods comprising the outer shell of the assembled bundle of parallel rods.

119. The method of claim 118 wherein the second structural materials is a catalyst powder.

120. The method of claim 119, wherein the channel-forming filler material of said second mixture is a substance selected from among melamine and a polymer.

121. The method of claim 36 wherein certain of the respective bundles contain parallel channels of different diameter than the diameter of the channels of certain other bundles.

122. The method of claim 39 wherein the channels of the alternately transverse layers are of different diameter.

123. The method of claim 55 wherein the powdered metal is an alloy powder.

124. The method of claim 56 wherein the powdered metal is an alloy powder.

125. The method of claim 123 wherein the structural material is FeCrAlY and is formed from the corresponding elemental metal powder mixture by mixing the appropriate stiochiometric ratio of the elemental metal powders and forming the alloy during or after sintering.

126. The method of claim 125 wherein the FeCrAlY is a catalyst support.

127. The method of claim 126 wherein a catalyst is coated on the FeCrAlY catalyst support.

* * * * *